United States Patent

Bender

[11] 4,231,954
[45] Nov. 4, 1980

[54] DANE SALT AND PROCESS FOR PREPARING AMINOPENICILLINS THEREFROM

[75] Inventor: Reinhold H. W. Bender, Kennett Square, Pa.

[73] Assignee: American Home Products Corporation, New York, N.Y.

[21] Appl. No.: 31,890

[22] Filed: Apr. 20, 1979

[51] Int. Cl.³ .................. C07C 121/60; C07D 499/00
[52] U.S. Cl. ........................ 260/465 D; 260/501.11; 260/501.12; 260/239.1; 562/426; 562/437
[58] Field of Search .................. 260/501.11, 501.12, 260/465 D; 562/437, 426

[56] References Cited

U.S. PATENT DOCUMENTS

| | | | |
|---|---|---|---|
| 3,316,247 | 4/1967 | Fosker et al. | 260/239.1 |
| 3,325,479 | 6/1967 | Fosker et al. | 260/239.1 |
| 3,406,185 | 10/1968 | Patchett et al. | 562/437 |
| 3,576,855 | 4/1971 | Duonch et al. | 562/437 |
| 3,654,266 | 4/1972 | Robinson | 260/239.1 |
| 3,868,364 | 2/1975 | Ishimaru et al. | 260/239.1 |
| 4,123,611 | 10/1978 | Ishimaru et al. | 562/561 |
| 4,128,547 | 12/1978 | van der Drift et al. | 260/239.1 |

FOREIGN PATENT DOCUMENTS

| | | |
|---|---|---|
| 867414 | 9/1978 | Belgium . |
| 142416 | 11/1970 | Netherlands . |
| 476758 | 9/1969 | Switzerland . |
| 1339605 | 12/1973 | United Kingdom . |
| 1347979 | 2/1974 | United Kingdom . |

OTHER PUBLICATIONS

Ishimaru et al., Chem. Absts., 79, 78822(c), 1973.
Dane et al., Chem. Ber., 98, 789 (1965).
Laplex, Chem. Absts., 84, 44031(z), 1976.

*Primary Examiner*—G. T. Breitenstein
*Attorney, Agent, or Firm*—George Tarnowski

[57] ABSTRACT

Amide-type Dane salts having the formula:

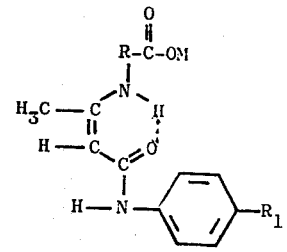

wherein R is a group of the formula:

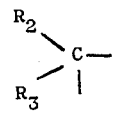

wherein $R_2$ is hydrogen and $R_3$ is phenyl or substituted phenyl, $R_1$ is cyano or nitro, and M is hydrogen, an alkali metal or a triloweralkylamine are disclosed, as well as a process for preparing α-aminopenicillins from these salts and 6-APA.

5 Claims, No Drawings

DANE SALT AND PROCESS FOR PREPARING AMINOPENICILLINS THEREFROM

BACKGROUND OF THE INVENTION

The α-aminopenicillins, such as for example ampicillin, amoxicillin and cyclacillin, are very useful antibiotics which are widely used against a large number of gram-positive and gram-negative micro-organisms.

These semisynthetic penicillins have been prepared by various processes and there is a large body of literature dealing with these methods of preparation. A number of patent applications and patents disclose preparations in which 6-aminopencillanic acid is acylated with mixed anhydrides derived from the modified Dane salts of D-2-amino-(substituted)-acetic acid. Such methods of preparation are described in Netherlands Pat. No. 142,416; British Pat. No. 1,347,979 and U.S. Pat. Nos. 3,316,247, 3,325,479 and 4,123,611.

The Dane salts described in the literature can be either of the ester-type or the amide-type, i.e. in Dane salts having the general formula:

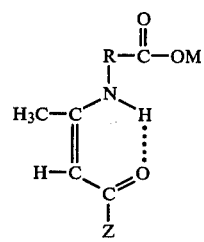

wherein

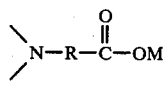

represents an amino acid residue and M is hydrogen or an alkali metal, and when Z is an alkoxy group they are of the ester-type, while when Z is an amino or substituted amino group they are of the amide-type.

The ester-type Dane salts have been widely used in preparing α-aminopenicillins and one process employing these salts is described in U.S. Pat. No. 4,128,547. In the general Dane salt/6-aminopenicillanic acid acylation process, the N-protected aminopenicillin which is formed during the acylation step is hydrolyzed to yield the desired α-aminopenicillin and, in the case of ester-type Dane salts, a β-ketoester. These β-ketoesters are generally liquids which are separated from the water-soluble α-aminopenicllin salts by extraction in an organic solvent. However, this is a significant disadvantage of the ester-type Dane salts since the β-ketoesters are not readily recovered from solution and so recycle of these β-ketoesters for the preparation of further starting Dane salts is not practicable on a commercial scale.

The amide-type Dane salts, in which Z is an amino or substituted amino group, are not as well-known as the ester-types and have not received as much attention in the literature. The amide-type Dane salts in which Z is the group $NR_1R_2-$, wherein $R_1$ is hydrogen and $R_2$ is o- or p-methoxyphenyl have been described in Chem. Ber., 98, 789 (1965) and Belgian Pat. No. 824,158. Those in which $R_1$ is hydrogen and $R_2$ is phenyl or halophenyl have been described in Swiss Pat. No. 476,758 and British Pat. No. 1,339,605. Those in which $R_1$ and $R_2$ are both alkyl or $NR_1R_2$ are morpholino have been described in Netherlands Pat. No. 142,416, British Pat. No. 1,339,605 and U.S. Pat. No. 4,123,611. Those in which $R_1$ and $R_2$ are both aryl or in $NR_1R_2$ form a piperidino ring have been described in U.S. Pat. No. 4,123,611. These known amide-type Dane salts, however, have the disadvantage that they generally give poor yields of the final product α-aminopenicillins.

The prior art also shows that it is advantageous to protect the carboxylic acid group or both the amino and carboxylic acid groups of 6-aminopenicillanic acid before it is reacted with the desired Dane salt. The proposed useful protecting groups include the trialkylhalosilanes, as in British Pat. No. 1,339,605 and U.S. Pat. No. 4,128,547; dialkyldihalosilanes, as in U.S. Pat. No. 3,654,266; and silanes having at least one C—O—Si bond in the molecule, such as in U.S. Pat. No. 3,868,364. However, the protection of the carboxylic group or carboxylic and amino groups of 6-aminopenicillanic acid has not produced an improvement in the overall prior art processes' economics, since their other disadvantages, such as low yield, complexity of procedure and low-purity of final product are not overcome thereby.

BRIEF DESCRIPTION OF THE INVENTION

It has been found now that the disadvantages of the prior art processes can be overcome by the novel amide-type Dane salts and the improved process of the present invention.

The novel amide-type Dane salts of the present invention, which have the general formula:

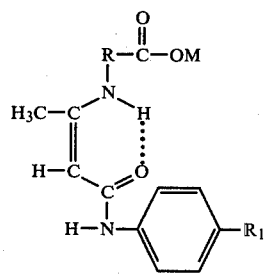

wherein R is a group of the formula:

wherein $R_2$ is a hydrogen atom and $R_3$ is phenyl or substituted phenyl; $R_1$ is cyano or nitro and M is hydrogen, an alkali metal or a triloweralkylamine are superior to the known ester-type and amide-type Dane salts for the preparation of α-aminopenicillins.

According to the improved process of the invention, α-aminopenicillins having the formula:

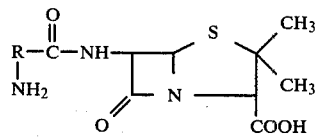

where R is defined as hereinbefore, are prepared by reacting a derivative of 6-aminopenicillanic acid in a substantially anhydrous, inert, water-insoluble organic solvent at a temperature at or below −20° C. with at least a 0.8 molar amount of a mixed anhydride prepared by reacting an amide-type Dane salt (II) with an alkyl-chlorocarbonate in the presence of a catalyst in an inert, water-insoluble organic solvent, hydrolyzing the resulting N-protected aminopenicillin to yield an α-aminopenicillin and a β-ketoamide, and recovering the α-aminopenicillin and optionally, the β-ketoamide.

The term "lower alkyl" refers to groups in which the alkyl moiety has a carbon atom content of $C_1$-$C_4$.

DETAILED DESCRIPTION OF THE INVENTION

The novel amide-type Dane salts of Formula II include those in which the grouping >N—R—COOH represents an amino acid residue, especially that of an amino acid in which the amino group is at the α-position to the carboxyl group, which can be represented by the formula:

wherein $R_2$ is hydrogen and $R_3$ is methylthiophenyl, phenyl, nitrophenyl, aminophenyl, hydroxyphenyl, alkoxyphenyl, or halogenophenyl. The preferred amino acids and thus amino acid residues are those in which $R_3$ is phenyl, hydroxyphenyl or alkoxyphenyl. Most preferred are those in which $R_3$ is phenyl or p-hydroxyphenyl.

The $R_1$ substituents in Formula II include cyano and nitro, with nitro being especially preferred. It has been found that when $R_1$ is an electron-withdrawing group, such as the cyano and nitro groups, rather than an electron-donating group, such as alkoxy, under identical conditions the yields of final product α-aminopenicillin are greatly enhanced.

The Dane salts of the invention include those in which M is hydrogen, an alkali metal, or a triloweralkylamine. The most preferred being the sodium salt.

The novel Dane salts are conveniently prepared by condensing an α-amino acid (VI) or a salt thereof with a β-ketoamide (VII), one method of effecting this condensation being described by Dane et al. (Angew. Chem., 1962, 74, 873).

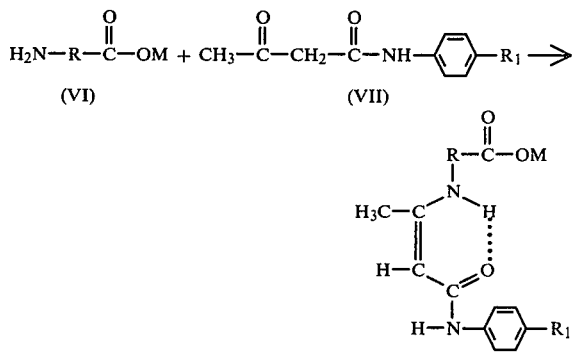

The β-ketoamides used in the above condensation are commercially available or they can be conveniently prepared according to the diketene acetoacetylation reaction described by Zavialov et al. (Tetrahedron, 1966, 22, 2003).

In accordance with the improved process of the invention, 6-aminopenicillanic acid, in suitably protected form is reacted with a mixed anhydride formed from a Dane salt of the invention.

The mixed anhydride is prepared by reacting a Dane salt of Formula II, preferably the sodium salt, with an alkyl or aralkyl chlorocarbonate in the presence of a catalyst in a water-insoluble solvent. The useful chlorocarbonates include methyl chloroformate, ethyl chlorocarbonate, isobutyl chloroformate isopropyl chloroformate, benyl chloroformate and the like, with ethyl chloroformate being preferred.

The preferred catalysts have the formula:

where X is a hydrogen atom or an alkyl, substituted alkyl, phenyl, substituted phenyl, or carboxyl group; Y is a hydrogen atom or a lower alkyl group or X and Y together represent any one of the divalent radicals ethylene, substituted ethylene, trimethylene, substituted trimethylene, —$CH_2OCH_2$— or —$CH_2N(CH_3)CH_2$—. Examples of such catalysts are N-methylmorpholine and N,N-dimethybenzylamine with N-methylmorpholine being most preferred.

The water-insoluble solvent used in the mixed anhydride preparation may be methylene chloride to which dimethylformamide, sulfolane, tetrahydrofuran, N-methylpyrrolidone, 1,4-dioxane, acetonitrile, dimethylacetamide or tetramethylurea or a mixture thereof is added as a co-solvent or methylisobutylketone, to which one or more of the afore-mentioned co-solvents may optionally be added. The preferred solvent is methylene chloride with at least 10% by volume of a co-solvent. It is also preferable to avoid a mixture of solvents as the co-solvent.

The mixed anhydride preparation is preferably carried out at a temperature of −10° C. or below, most preferably at a temperature of about −20° to about −30° C.

The 6-aminopenicillanic acid (6-APA) is reacted with the mixed anhydride in the form of a derivative such as an alkali metal or alkaline earth salt, as a derivative of a substituted amine or as a silyl derivative in which the silyl group protects the 6-APA carboxylic acid group or both the carboxylic acid and amino groups. The preferred amine salts are the tertiary amine salts, especially triethylamine. However, since the β-lactam ring of 6-APA is prone to cleavage in an aqueous medium, and since such cleavage results in the need for complicated steps to separate and refine the final product, it is most preferable to carry out the acylation reaction in a non-aqueous solvent system and with the 6-APA suitably protected. Accordingly, in the process of the invention, the 6-APA is reacted with a silylating agent which provides good solubility in many organic solvents and at the same time protects the carboxylic acid group or both the carboxylic acid and amino groups of 6-APA. Moreover, after the acylation reaction, the silyl protecting group is readily removed.

The useful silylating agents include halotrialkylsilanes, dihalodialkylsilanes, halotrialkoxysilanes, dihalodialkoxysilanes, halodialkylalkoxysilanes, halodialkoxyalkylsilanes or corresponding aryl or aralkyl silanes. The preferred silylating agents are dihalodialkylsilanes and halotrialkylsilanes having the formula:

(IX)

wherein $R_1$, $R_2$, and $R_3$ are each lower alkyl cycloalkyl, benzyl, or aryl such as methyl, ethyl, cyclopentyl, cyclohexyl, benzyl or phenyl, or one of $R_1$, $R_2$, or $R_3$ is defined as X, and X is any group readily displaced by a nucleophilic reaction involving a carboxylic acid or its salts or an amino group. X is preferably a halogen atom, most preferably chlorine, but good results can also be obtained with compounds such as trimethylsilylacetamide, bis(trimethylsilyl)acetamide, hexamethyldisilazene and bis-trimethylsilylurea. The most preferred silylating agents are trimethylchlorosilane or dimethyldichlorosilane.

The silylation is carried out in a dry, inert, water-insoluble solvent, preferably dry methylene chloride, and in the presence of a tertiary amine. The silylation is performed using about 2 equivalents of a tertiary amine, preferably triethylamine, with the amount of silylating agent varying with the type of agent employed. Thus, with trialkylchlorosilanes, it is preferable to use an amount between 1 and 3 equivalents, while with dialkyldichlorosilanes, it is preferable to use an amount between 0.5 and 1 equivalent. The silylation is carried out at a temperature between about 15° to about 40° C.

The acylation is carried out by cooling the mixed anhydride solution to a temperature of about −20° to about −35° C., and rapidly adding thereto a cooled solution of a 6-APA derivative, most preferably in the form of a silylated derivative. It is preferable to use the mixed anhydride in an amount of at least 0.8 equivalents based on the 6-APA derivative, the useful range being 0.8–1.2 equivalents. The addition is performed with stirring and the temperature is reduced to about −20° to −35° C. Stirring is continued for a further 0.5 to 5 hours. The intermediate N-protected aminopenicillin resulting from this acylation can then be hydrolyzed in situ.

The N-protected aminopenicillin is then hydrolyzed by mixing the solution with a dilute solution of an organic acid, or an inorganic acid, such as dilute aqueous hydrochloric acid, at a temperature of about 10° to about −5° C. and at a pH of about 0.9–2.0. The mixture is stirred at the same temperature for up to 2 hours.

The aqueous and organic layers are allowed to separate, the aqueous layer containing the desired final product, as its organic or inorganic salt, is washed with an inert, water-insoluble organic solvent, such as ethyl acetate, methylisobutyl ketone or methylene chloride. The organic layer, containing the β-ketoamide, liberated from the N-protected aminopenicillin during hydrolysis, is washed with water and the wash waters are extracted and added to the washed aqueous layer. The aqueous layer is adjusted to the isoelectric point of the αaminopenicillin, allowed to crystallize and the desired final product α-aminopenicillin recovered.

The organic layer and the organic solvent washes of the aqueous layer are combined, filtered and concentrated to dryness. The residue is stirred in water and concentrated hydrochloric acid at 30°–40° C. for 0.5 hour and then at a temperature of about 3° to about 5° C. for 2 hours. The liberated β-ketoamide crystallizes and is recovered. The latter, which is recovered at a high degree of purity and in quantitative yields, is readily recycled for the preparation of further starting amide-type Dane salts.

The improved process of the invention, using novel amide-type Dane salts, advantageously give high yields of α-aminopenicillins at the required high degree of purity with minimal losses of 6-APA due to β-lactam ring cleavage and any concomitant crystallization of 6-APA along with product α-aminopenicillin. The high concentrations of starting, intermediate, and final materials allows for a high throughput. Moreover, the absence of the hitherto usual organic solvent vacuum distillation step subsequent to acylation results in less product degradation and the elimination of the costs involved in vacuum distillation. The recyclable nature of the β-ketoamide liberated during hydrolysis provides a very significant advantage to process economics, as the readily recovered crystalline β-ketoamides are re-used in further preparation of the amide-type Dane salts.

The following examples illustrate preferred embodiments of the invention, but the invention is not intended to be limited thereby.

EXAMPLE 1

D-2-(4-Hydroxyphenyl)-N-[1-methyl-2-(4-nitrophenylcarbamoyl)vinyl]glycine, sodium salt A 5 L. 4-neck flask, fitted with a stirrer, thermometer, reflux condenser, nitrogen inlet and drying tube, is charged with 2.6 L. of methanol and 117 g. (2.88 moles) of sodium hydroxide pellets. The mixture is heated to reflux and stirred until all sodium hydroxide is dissolved. Then 457 g. (2.74 moles) of D(−)-p-hydroxyphenylglycine is added, followed by 640 g. (2.88 moles) of p-nitroacetoacetanilide. The reaction mixture is reheated and kept at reflux for 30 minutes. After removal of the heat source, the stirring is continued for 60 minutes and then the mixture is stirred for 3 hours at 3° C. The precipitate is collected by filtration and washed with 0.5 L. of methanol. The product is dried in an air oven at 4° C. overnight to obtain 927 g. (86.1% yield) of the title compound. Upon concentration of mother liquor and wash, a further 129 g. (12%) of product is isolated. Melting point: 260°–265° C. dec.

EXAMPLE 2

D-2-(4-Hydroxyphenyl)-N-[1-methyl-2-(4-nitrophenylcarbamoyl)vinyl]glycine, potassium salt The title compound is prepared in 89.3% yield by a procedure similar to Example 1. Melting point: 220°–245° C. dec.

EXAMPLE 3

D-N-[2-(4-Cyanophenylcarbamoyl)-1-methylvinyl]-2-(4-hydroxyphenyl)glycine, potassium salt The title compound is prepared in a similar manner as Example 1 in 78.8% yield using p-cycanoacetoacetanilide. When methanol is replaced by ethanol, the title compound is obtained in 92.3% yield. Melting point: 250°–255° C. dec.

EXAMPLE 4

D-N-[2-(4-Cyanophenylcarbamoyl)-1-methylvinyl]-2-(4-hydroxphenyl)glycine, sodium salt The title compound is prepared in a similar manner as Example 1, using sodium hydroxide and methanol in 55.3% yield. Melting point: 230°–240° C. dec.

EXAMPLE 5

D-N-[1-Methyl-2-(4-nitrophenylcarbamoyl)vinyl]-2-phenylglycine, sodium salt

The title compound is prepared in a similar manner as Example 1 using D(−)phenylglycine, methanol and sodium hydroxide in 81.4% yield. Melting point: 220°–230° C. dec.

EXAMPLE 6

D-N-[1-Methyl-2-(4-nitrophenylcarbamoyl)vinyl]-2-phenylglycine, potassium salt

The title compound is prepared in a similar manner as as Example 1, using potassium hydroxide, in 86% yield. Melting point: 170°–178° C. dec.

EXAMPLE 7

6-[(−)-α-amino-p-hydroxyphenylacetamido]-penicillanic acid, trihydrate

A. Preparation of Mixed Anhydride

A 5 L. 4-neck flask, fitted with a stirrer, low temperature thermometer with "thermowatch", nitrogen inlet and drying tube, is charged with 600 ml. of methylene chloride, 120 ml. of dimethylacetamide (with a 4–5% H$_2$O content), 0.7 ml. of N-methylmorpholine and 100 g. (0.254 mole) of D-2-(4-hydroxyphenyl)-N-[1-methyl-2-(4-nitrophenylcarbamoyl)vinyl]glycine sodium salt prepared according to Example 1. The mixture is cooled, with stirring, to −30° C. and 28.4 g. (0.26 mole) of ethyl chloroformate is added all at once. The temperature is allowed to rise to −23° C. and the mixture is stirred at −23° C. for 1 hour.

B. Preparation of 6-APA Derivative

To a 1 L. 4-neck flask, fitted with a stirrer, thermometer, nitrogen inlet and dropping funnel, is charged 540 ml. of methylene chloride, 54 g. (0.25 mole) of 6-aminopenicillanic acid (6-APA) and 50.5 g. (0.5 mole) of triethylamine. 35.7 g. (0.33 mole) of trimethylchlorosilane is added, with vigorous stirring, over a period of 20 minutes, allowing the temperature to rise to 35° C. Stirring is continued, allowing the temperature to drop to room temperature.

C. Preparation of 6-[D(−)-α-amino-p-hydroxyphenylacetamido]-penicillanic acid, trihydrate After cooling the mixed anhydride mixture of A above to −45° C. the silylated 6-APA mixture of B above is added all at once while the temperature rises to −30° C. The resulting mixture is stirred for 5 hours at −30° C. The mixture is allowed to warm to −10° C. and 700 ml. of water are added; the temperature rises to 5° C. The N-protected α-aminopenicillin in the resulting mixture is then hydrolyzed in situ. Thus, the pH of the mixture is ajusted to 1.5 with concentrated hydrochloric acid and the mixture is stirred for 15 minutes at 5° C. The layers are separated and the lower, organic layer is re-extracted with 100 ml. of water. The combined aqueous phases are washed with 250 ml. of ethyl acetate and then filtered through Celite.

The pH of the aqueous filtrate is adjusted to 5.4 at 5° C. with concentrated ammonia. The resulting thick slurry is stirred overnight at 0°–5° C. The product is filtered on a Buchner funnel, washed with aqueous acetone and dried to constant weight at 40° C. to afford 87.1 g. (83% of theory) of title compound. The K.F. analysis gave 14.2% against 12.9% H$_2$O of theory, iodometric assay, 855 mcg/mg. In another experiment the yield is 83.3 g. (79% of theory), K.F. 14.3% (theory 12.9% H$_2$O), iodometric assay, 828 mcg/mg.

D. Recovery of p-Nitroacetoacetanilide

The organic layer from C above is concentrated to dryness. The oily residue is stirred in 200 ml. water and 50 ml. concentrated hydrochloric acid at 30°–40° C. for 0.5 hour and then at 3°–5° C. for 2 hours. 53 g. (96.5% of theory) of crude p-nitroacetoacetanilide, having a melting point of 105°–110° C., is recovered. This crude material is used to prepare D-2-(4-hydroxyphenyl)-N-[1-methyl-2-(4-nitrophenylcarbamoyl)vinyl]glycine, sodium salt in the same way and with the same yield as in Example 1.

EXAMPLE 8

6-[D(−)-α-aminophenylacetamido]penicillanic acid, anhydrous

6-[D(−)-α-aminophenylacetamido]penicillanic acid (ampicillin) naphthalene sulfonic acid salt is prepared by a procedure similar to that in Example 7, except that 96 g. (0.25 mole) of D-N-[1-methyl-2-(4-nitrophenylcarbamoyl)vinyl]glycine sodium salt prepared according to Example 5 is used with 500 ml. of methylene chloride and 50 ml. of dimethylacetamide (with a 4–5% H$_2$O content). To the final aqueous ampicillin solution is added 100 ml. of ethyl acetate and 200 g. of aqueous β-naphathalene sulfonic acid solution (29% weight/volume) while the pH is adjusted to 1.2 at 5°–10° C. by the concurrent addition of triethylamine. The resulting thick slurry is stirred overnight at 0°–5° C. The product is filtered on a Buchner funnel and washed with water and ethyl acetate. The yield is 203.8 g. wet ampicillin β-naphthaline sulfonic acid salt. Drying a sample indicates a yield of 123.5 g. or 89% of theory.

The wet filter cake is treated with one equivalent of triethylamine in 85% aqueous isopropanol at 65° C. for 30 minutes, filtered and dried to give 67.5 g. of anhydrous ampicillin for an overall yield of 77% based on 6-APA, iodometric assay, 1011 mcg/mg.

In another experiment the yield of anhydrous ampicillin is 65.6 g. for an overall yield of 75% based on 6-APA, iodometric assay, 999 mcg/mg.

EXAMPLE 9

6-[D(−)-α-amino-p-hydroxphenylacetamido]-penicillanic acid, trihydrate

The procedure of Example 7 is followed, except that the trimethylchlorosilane is replaced by 21.3 g. (0.165 mole) of dimethyldichlorosilane. The yield is 84.3 g. (80% of theory), K.F. 13.9% (12.9% H$_2$O of theory), iodometric assay, 862 mcg/mg.

EXAMPLE 10

6-[D(−)-α-aminophenylacetamido]-penicillanic acid, anhydrous

The procedure of Example 8 is followed, except that the trimethylchlorosilane is replaced by 21.3 g. (0.165 mole) of dimethyldichlorosilane. The yield of title compound is 69 g. for an overall yield of 79%, iodometric assay, 992 mcg/mg.

EXAMPLE 11

6-[D(—)-α-amino-p-hydroxyphenylacetamido]-penicillanic acid, trihydrate

The procedure of Example 7 is followed, except that the D-2-(4-hydroxyphenyl)-N-[1-methyl-2-(4-nitrophenylcarbamoyl)vinyl]glycine sodium salt is replaced with 97.5 g. of D-N-[2-(4-cyanophenylcarbamoyl)-1-methyl-vinyl]-2-(4-hydroxyphenyl)glycine, potassium salt prepared according to Example 3 and the trimethylchlorosilane is replaced with 21.3 g. (0.165 mole) of dimethyldichlorosilane. The yield of title compound is 65.5 g. (62.4% of theory).

The organic layer is treated as in Example 7D to yield 45 g. of p-cyanoacetoacetanilide (90% of theroy) having a melting point of 119°–120° C.

What is claimed is:

1. A compound having the formula:

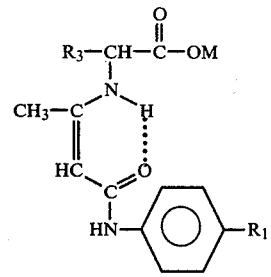

wherein $R_1$ is cyano or nitro; $R_3$ is phenyl, methylthiophenyl, nitrophenyl, aminophenyl, hydroxyphenyl, alkoxyphenyl in which alkoxy is of 1–4 carbon atoms or halogenophenyl; and M is hydrogen, an alkali metal or a triloweralkylamine.

2. The compound of claim 1, wherein $R_3$ is phenyl.
3. The compound of claim 1, wherein $R_3$ is p-hydroxyphenyl.
4. The compound of claim 1, wherein $R_1$ is cyano.
5. The compound of claim 1, wherein $R_1$ is nitro.